US008382834B2

(12) United States Patent
Prescott

(10) Patent No.: US 8,382,834 B2
(45) Date of Patent: Feb. 26, 2013

(54) INDUCTION HEATER SYSTEM FOR SHAPE MEMORY MEDICAL IMPLANTS AND METHOD OF ACTIVATING SHAPE MEMORY MEDICAL IMPLANTS WITHIN THE MAMMALIAN BODY

(75) Inventor: Anthony D. Prescott, Arlington, TN (US)

(73) Assignee: Enteroptyx, Memphis, TN (US)

(*) Notice: Subject to any disclaimer, the term of this patent is extended or adjusted under 35 U.S.C. 154(b) by 297 days.

(21) Appl. No.: 12/758,344

(22) Filed: Apr. 12, 2010

(65) Prior Publication Data

US 2011/0251687 A1  Oct. 13, 2011

(51) Int. Cl.
A61F 2/18 (2006.01)
A61F 7/00 (2006.01)

(52) U.S. Cl. ............................................ 623/10; 607/96

(58) Field of Classification Search ............... 606/27–32, 606/41–50; 607/96–102, 113–114; 623/9–10
See application file for complete search history.

(56) References Cited

U.S. PATENT DOCUMENTS

| 4,638,571 A | 1/1987 | Cook |
| 5,025,799 A | 6/1991 | Wilson |
| 5,143,085 A | 9/1992 | Wilson |
| 5,160,828 A | 11/1992 | Olsen |
| 5,211,183 A | 5/1993 | Wilson |
| 5,290,289 A | 3/1994 | Sanders et al. |
| 5,378,879 A | 1/1995 | Monovoukas |
| 5,741,249 A | 4/1998 | Moss et al. |
| 6,080,160 A | 6/2000 | Chen et al. |
| 6,238,421 B1 * | 5/2001 | Gunther et al. ................. 607/13 |
| 6,255,634 B1 | 7/2001 | Bowers |
| 6,377,775 B1 | 4/2002 | Nakayama et al. |
| 6,397,107 B1 | 5/2002 | Lee et al. |
| 6,485,507 B1 | 11/2002 | Walak et al. |
| 6,511,508 B1 * | 1/2003 | Shahinpoor et al. ........... 623/4.1 |
| 6,554,861 B2 | 4/2003 | Knox et al. |
| 6,576,878 B2 | 6/2003 | Thorpe et al. |

(Continued)

FOREIGN PATENT DOCUMENTS

| EP | 0369624 | 5/1990 |
| EP | 1913887 A1 | 4/2008 |

(Continued)

OTHER PUBLICATIONS

Cylindrical Tissue Model for Magnetic Field Stimulation of Neurons: Effects of Coil Geometry, Karu P. Essele and Maria A. Stuchly, IEEE Transactions on Biomedical Engineering, vol. 42, No. 9, Sep. 1995, pp. 934-941.

(Continued)

*Primary Examiner* — Suzette J Gherbi
(74) *Attorney, Agent, or Firm* — Gordon & Jacobson, PC

(57) ABSTRACT

A method of altering a medical implant having a shape memory portion includes the use of a probe having a tip provided with an induction coil. The induction coil is electrically coupled to an induction power supply. The induction coil is inserted into the mammalian body. The power supply is activated at a suitable frequency to cause the induction coil to generate a magnetic field, wherein such magnetic field induces eddy currents in the shape memory portion of the implant which are sufficient to heat the shape memory portion of the implant to a phase transformation temperature to effect shape change of the implant.

17 Claims, 5 Drawing Sheets

U.S. PATENT DOCUMENTS

| | | | |
|---|---|---|---|
| 6,677,561 B1 | 1/2004 | Koppinen et al. | |
| 6,850,804 B2 | 2/2005 | Eggers et al. | |
| 7,087,869 B2 | 8/2006 | Eguchi et al. | |
| 7,482,559 B2 | 1/2009 | Cao et al. | |
| 7,588,565 B2 * | 9/2009 | Marchitto et al. | 606/27 |
| 7,955,386 B2 * | 6/2011 | Reitan et al. | 623/10 |
| 8,206,444 B2 * | 6/2012 | Reitan et al. | 623/10 |
| 2005/0197685 A1 * | 9/2005 | Russell | 607/115 |
| 2009/0046146 A1 | 2/2009 | Hoyt | |
| 2009/0076597 A1 | 3/2009 | Dahlgren et al. | |
| 2009/0218321 A1 * | 9/2009 | Ashman | 219/50 |
| 2010/0069781 A1 * | 3/2010 | Johansen et al. | 600/547 |
| 2011/0060214 A1 * | 3/2011 | Makower | 600/424 |
| 2012/0136433 A1 * | 5/2012 | Marmureanu et al. | 623/2.11 |
| 2012/0157984 A1 * | 6/2012 | Thapliyal et al. | 606/28 |
| 2012/0172680 A1 * | 7/2012 | Gelfand et al. | 600/301 |

FOREIGN PATENT DOCUMENTS

FR 2365267 4/1978

OTHER PUBLICATIONS

Design of Induction Heating Coils, Electroheat Technologies—Induction Heating Equipment, Submitted as Prior Art.

Turnkey Induction Heating Solutions, Induction Atmospheres, available at http://www.inductionatmospheres.com/induction_heating.html, Submitted as Prior Art.

Medical Applications for Precision Induction Heating; Brochure, Ambrell, 2009, available at http://www.ameritherm.com/PDFs/411-0039-01.pdf.

* cited by examiner

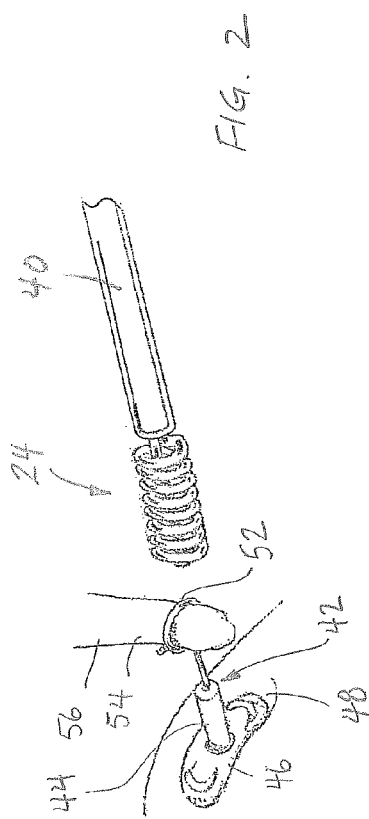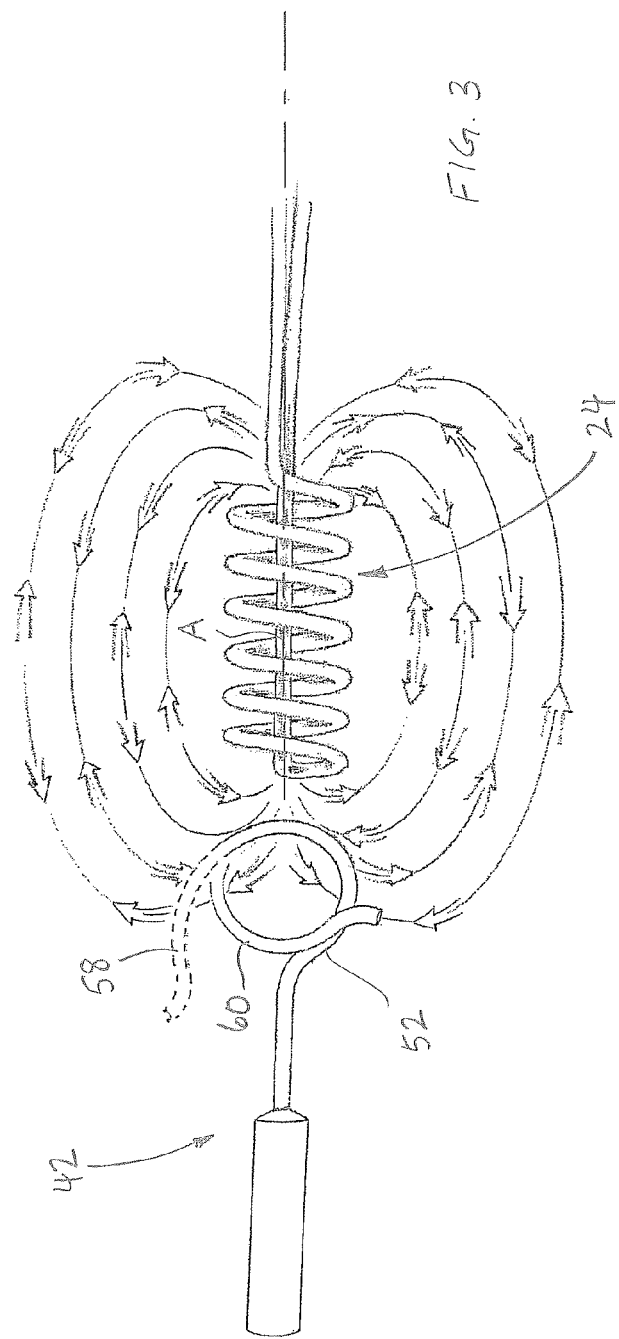

INDUCTION HEATER SYSTEM FOR SHAPE MEMORY MEDICAL IMPLANTS AND METHOD OF ACTIVATING SHAPE MEMORY MEDICAL IMPLANTS WITHIN THE MAMMALIAN BODY

BACKGROUND OF THE INVENTION

1. Field of the Invention

This invention relates broadly to an induction heater introducible into a mammalian body and methods of activating medical implants. More particularly, this invention relates to devices and methods for applying energy to a shape memory medical implant to heat the medical implant to a transition temperature so as to cause the implant to assume an altered configuration.

2. State of the Art

It is known to manufacture medical implants for various applications from a shape memory metal alloy such as Nitinol. When a shape memory medical implant is heated above a phase transformation temperature, a change from the martensitic crystalline structure to the austenitic crystalline structure is induced to cause the implant to revert to a shape that has been heat-trained in the implant during the manufacturing process.

In one specific example, it is known to manufacture otological prostheses from shape memory nickel titanium alloy, and use the shape memory property to cause the implant, upon heating to the phase transformation temperature, to assume an implanted configuration in which a portion of the implant bends and engages an ossicular structure to secure the implant within the ossicular chain. Various devices and methods are known for heating shape memory prosthesis for the middle ear ossicles.

For example, U.S. Pat. No. 6,554,861 to Knox discloses the use of a laser device to generate a laser beam which is directed at a portion of a stapedial prosthesis to cause a bight portion of the prosthesis to bend about an incus to anchor the prosthesis in place. However, the laser must be used with high accuracy and with caution, because if the high energy beam is misdirected off the prosthesis and onto tissue, severe damage to the tissue can occur.

It is also known to use an electrocautery probe to heat a shape memory ossicular prosthesis via conduction across an air gap. However, because the high heat generated by a cautery probe is non-directional, it can also cause collateral damage to surrounding tissue.

SUMMARY OF THE INVENTION

In accord with the invention, a device is provided to activate a shape memory metal alloy medical implant in a mammalian body. The device is particularly adapted in size for temporary insertion within the human body and particularly within the small confines of the middle ear that may be required, e.g., with the activation of a shape memory middle ear implant.

In accord with an embodiment of the invention, the device includes a handle, a probe extending from the distal end of the handle, and an induction coil located at the distal tip of the probe. The coil preferably has a dimension transverse its longitudinal axis not exceeding 4 mm so that insertion into the middle ear or other small anatomical opening or cavity is facilitated. The device includes suitable connectors to electrically couple the coil to an alternating current induction power supply. The power supply sends alternating current through the coil, generating a magnetic field. The power supply is preferably capable of operating at a frequency of 300 kHz to 1 Mhz at under 100 watts. Upon activation of the power supply, the magnetic field generated by the coil induces eddy currents in an adjacent shape memory implant. This results in precise amounts of clean, localized heat in the implant without any physical contact between the coil and the implant and without the device causing collateral heating of the surrounding tissue. The implant is heated to a temperature of 75° C.-85° C. within preferably 5 seconds, and more preferably within 2 to 4 seconds, which is sufficient to cause phase transformation shape change of the implant in a surgically suitable timeframe. The induction power supply is activated via a foot pedal or a button on the handpiece.

Induction coils of various designs are provided for the probe, including coils which permit transverse induction heating of the implant. It is recognized that a coil has a geometry, and the geometry defines a boundary volume. In transverse induction heating, the boundary volume of the coil is not positioned about the shape memory implant, but rather only adjacent the coil. This allows a coil to be used that (1) has a relatively smaller geometry, (2) has a geometry which would not permit the shape change of the implant to occur within a relatively small boundary volume of a coil, and (3) can in some instances provide better visibility of the implant during a procedure.

Induction coils are also provided for the probe which maximizes the magnetic coupling between the coil and the implant so that the eddy currents induced in the implant are maximized. In addition, the coil defines a space through which the implant can undergo shape change.

Induction coils are also provided in conjunction with flux concentrator materials that shape the magnetic field in favorable configurations for inducing eddy currents in the implants.

According to another embodiment, an induction coil is provided about the distal portion of a speculum. The speculum has a distal end sized for insertion into the ear and a larger proximal end. When the distal end is inserted into the ear, the induction coil is located within coupling distance of an otological prosthesis ready for implantation.

According to another embodiment, an induction coil of a heating system is provided in conjunction with a mount adapted for external placement on the human body, e.g., over the temporal bone at the middle ear. The mount preferably includes a disc about which the coil extends and a ring surrounding the coil. The mount also includes a contact surface which may be provided with a removable adhesive to temporarily position the mount to the skin of the human body, e.g., over the temporal bone, in a hands-free manner.

According to a method of the invention, the coil of the induction heater system is placed within 10 mm of the implant, and more preferably within 5 mm of the shape memory metal alloy implant. According to a preferred method of the invention, the coil is at the distal end of the probe sized for temporary internal placement within the human body. The alternating current induction power supply, operating at 300 kHz to 1 MHz and preferably 100 W or less, is then activated to generate a magnetic field in the coil which, in turn, generates eddy currents in the implant. The eddy currents travel on the outer skin of the implant and generate heat sufficient to rapidly elevate the temperature of the implant to 75° C.-85° C.; i.e., preferably within 1 to 5 seconds, and more preferably in the range of 2 to 4 seconds, to result in heat induced, phase transformation, shape change of the implant. For implants of small dimension, such as for ossicular implants, the stated frequency range of the power supply is important to prevent the eddy currents on opposing surfaces of the implant from interfering with each other and cancelling each other out, and thereby preventing the implant from reaching the required phase transformation temperature in a suitable time.

Additional advantages of the invention will become apparent to those skilled in the art upon reference to the detailed description taken in conjunction with the provided figures.

BRIEF DESCRIPTION OF THE DRAWINGS

FIG. 2 illustrates the distal end of the probe of the heater in relation to a shape memory ossicular implant and the middle ear anatomy.

FIG. 3 illustrates coupling the magnetic field of a transverse induction coil to a shape memory ossicular implant.

DETAILED DESCRIPTION OF THE PREFERRED EMBODIMENTS

Figure 1:
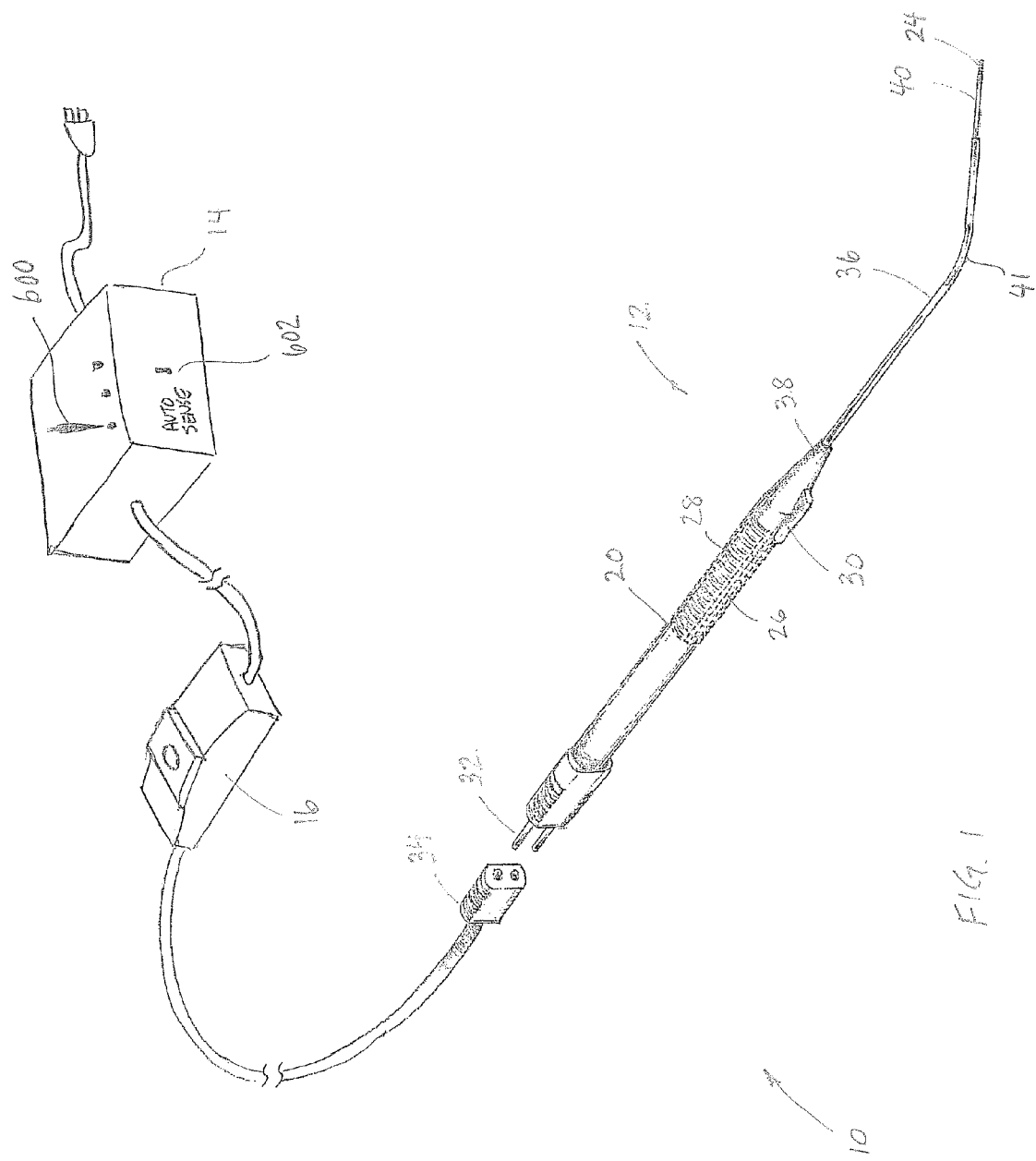
FIG. 1 is a first embodiment of an induction heater system according to the invention.

Turning now to FIG. 1, an induction coil heater system 10 for activating a shape memory metal alloy medical implant is shown. The system 10 includes a handpiece 12 and an AC, solid state, RF induction power supply 14, and an optional footswitch 16 for hands-free activation of the power supply 14.

The handpiece 12 includes a handle 20, a probe 22 and an induction coil 24. Importantly, the handpiece can be sterilized and readily constructed of materials that permit it to be a disposable single-use component. The handle 20 is preferably made from a non-conductive material such as plastic and has gripping structure, including by way of example, knurls 26, ridges 28, rubber, etc., to stabilize the handle in the hand of the surgeon, and a longitudinal ridge 30 to register the rotational orientation of the handle within the hand of the surgeon. The proximal end of the handle includes a male plug 32 for electrical coupling to a female plug 34 of the AC power supply 14. The ridge 30 may alternatively function as a power supply activation switch to activate the power supply rather than using the footswitch 16. A smaller diameter, longitudinal probe 36 extends from the distal end 38 of the handle, with the coil 24 located at the distal tip 40 of the probe. The probe 36 is bent along its length. The bend at 41 and a length of preferably 20 mm to 70 mm provide suitable clearance from the patient, and the probe diameter of preferably 2 mm permits surgeon visual access to the patient. The distal tip 40 is further stepped down in diameter to less than 2 mm, and preferably 0.3 mm to 1.5 mm, and preferably has a length of 70 mm to permit insertion through a natural orifice or a small surgical opening in the anatomy. The induction coil 24 at the distal tip 40 is electrically coupled via wires (not shown) extending through the handpiece 12 to the plug 32 such that the coil is coupled to the AC power source 14.

Referring to FIG. 2, the distal tip 40 is shown located within the middle ear, with the distal end of the coil provided adjacent a stapedial implant for restoring the ossicular chain. The implant 42 has a plastic, cylindrical first end 44 seated on a footplate 46 at the oval window 48 and a shape memory metal alloy second end forming a heat-activatable bight 52 that is adapted to bend about and attach to the long process 54 of the incus 56 when subject to a temperature above its phase transformation temperature.

Referring to FIG. 3, the coil 24 is made from metal conductor such as a solid copper wire provided with a surrounding insulating sheath. The wire has a diameter of 0.20 mm to 0.50 mm. In the shown embodiment, the coil 24 is generally cylindrical in form, with the electrode defining the coil extending in a helical configuration and, at the distal end, returning back alongside and external to the coil. The coil has three to fifteen complete spaced apart windings, and more preferably six to nine windings. The coil 24 has a longitudinal axis A and the generally cylindrical geometry defines a boundary volume. The inner diameter of the coil is preferably 0.5 mm to 3.0 mm, and the outer diameter preferably does not exceed 4.0 mm. A smaller diameter coil is more readily inserted into the body, particularly within a confined anatomical space. A larger diameter coil defines a visualization 'port' centered along axis A through which the implant can be visualized through the coil during the induction heating procedure described below. Embodiments having other shapes are described below.

When the AC power source is activated, a magnetic field is generated by the coil 24. The field lines of the magnetic field are shown by the arrows. When the coil is located such that the implant is within the magnetic field of the coil; i.e., the implant is coupled to the coil, eddy currents are induced in the implant. It is desirable to induce eddy currents that will rapidly elevate the subject portion of the implant to a phase transformation temperature of 75° C. to 85° C. within 5 seconds, and more preferably 1 to 4 seconds to cause the required shape change, e.g., from a first state open configuration shown at 58 in broken lines to a second state closed configuration shown at 60. Temperature elevation of the coil should remain below 70° C. when powered, and the implant temperature should not exceed the indicated temperature and time constraints in order to prevent tissue damage.

To efficiently heat thin films by inductive heating, it is preferred to limit induced eddy currents such that the opposing eddy currents from opposite sides of the film do not cancel each other out. Applicant has found that small medical implants, such as ossicular prosthesis 42 having a smaller diameter Nitinol wire shape memory portion 52, have similar inductive heating properties to thin films and therefore also benefit from heating in a manner in which opposing eddy currents do not cancel each other out; otherwise heating would be inefficient. However, it is also desirable to otherwise maximize the induced eddy currents to rapidly elevate the implant temperate so that shape change occurs quickly.

For example, with a 0.152 mm diameter Nitinol wire 52 (as is commonly used in shape memory ossicular prostheses) it is preferred that the eddy currents penetrate to a depth of 0.076 mm or less so that there is no interference and consequent cancellation of the eddy currents. The currents however should penetrate to almost 0.076 mm (but not exceed such depth) to maximize their heating power. The frequency of the power source to generate eddy currents at such depth ($\delta$, m) can be calculated as follows:

$$\delta = \sqrt{\frac{\rho}{\pi \cdot \mu \cdot f}},$$

where ρ is the resistivity (Ω, m), μ is the magnetic permeability (H/m), and f is the frequency (Hz) of the power source.

For Nitinol, the martensitic resistivity (ρ) is approximately 80 micro-ohms·cm and the magnetic permeability is approximately 1.002 (H/m). So, for Nitinol, the depth of penetration $$(m) = \delta = \sqrt{\frac{.008}{\pi \cdot 1.002 \cdot f}}.$$

TABLE 1

| Eddy Current Penetration Depth in Nitinol | |
| --- | --- |
| Depth (mm) | Frequency (kHz) |
| 0.07 | 500 |
| 0.065 | 600 |
| 0.06 | 700 |

As shown in Table 1, a frequency higher than 500 kHz provides a penetration depth of less than 0.076 mm.

In use, the handpiece 12 is manipulated to introduce the induction coil 24 at the end of the probe 36 into the body of the patient (FIGS. 1 and 3). The coil 24 is positioned relative to the implant 42 such that the implant is located external the boundary volume of the coil (FIG. 3). The power source 14 is then activated to generate the magnetic field in the induction coil 24 and, in turn, cause eddy currents in the implant 42. Within 1 to 5 seconds, and more preferably 2 to 4 seconds, the induced eddy currents heat the implant above the phase transformation temperature to change the implant from the martensitic crystalline structure to the austenitic crystalline structure and result in an altered shape configuration for the implant. As the implant is located outside the boundary volume of the coil 24, the heating is carried out via transverse induction. The handpiece 12 is then removed from the patient, disconnected from the power supply 14, and can be disposed. Alternatively, the handpiece 12 can be prepared for re-use via suitable cleaning and sterilization.

Figure 4:
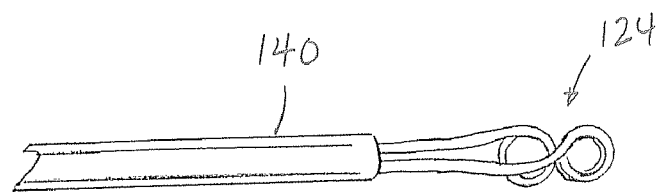
FIG. 4 is a side elevation view of the distal end of the probe of the heater system shown with a first alternate induction coil.

Turning now to FIG. 4, another embodiment of an induction coil 124 for a distal tip 140 at the end of the probe is shown. The coil is configured to extend in a Figure-8 arrangement. It has been shown that such an arrangement provides a magnetic field that is suitable for inducement of eddy currents in shape memory implants in the human body. The Figure-8 configuration has been shown to function similarly to the helical cylindrical coil described above.

Figure 5:
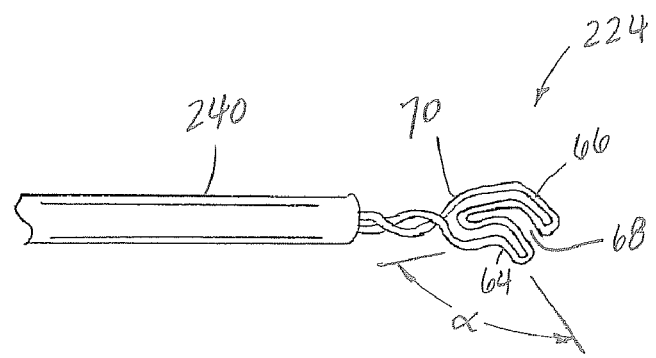
FIG. 5 is a side elevation view of the distal end of the probe of the heater system shown with a second alternate induction coil.

Referring now to FIG. 5, another embodiment of an induction coil 224 for a distal tip 240 at the end of the probe is shown. The coil is configured in the form of two longitudinally extending, parallel tines (or fingers) 64, 66 which together define a central space 68 therebetween. Each tine 64, 66 has an outline formed by the wire 70 of the coil 62. The tines 64, 66 are also preferably each formed with an angle α, such that the distal end of each tine is angled relative to the proximal end of the tine. Angle α is preferably 25°±10°. The configuration of the coil 224 permits the tines to be positioned on opposing sides of an implant, with the angle permitting movement of the field generating portion of the coil closer to the anatomy where the implant is located, and more particularly in an arrangement in which the tines are located one on each side of the implant. This allows the coil to be located in a closer coupling configuration with the implant without interference with the anatomy and also allows the implant to move through the tines as it deforms upon shape change.

Figure 6:
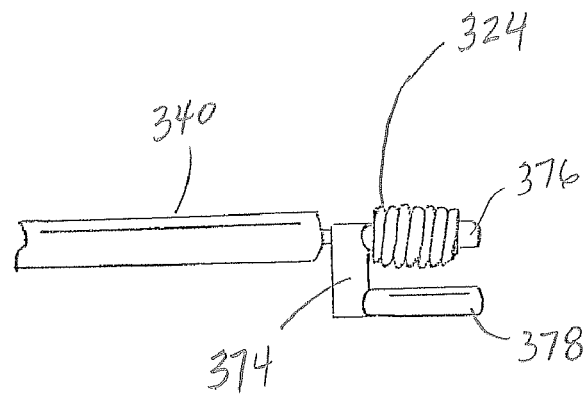
FIG. 6 is a side elevation view of the distal end of the probe of the heater system shown with a second alternate induction coil.

Turning now to FIG. 6, another embodiment of an induction coil 324 for a distal tip 340 at the end of the probe is shown. A helically wound coil 324 is mounted on a U-shaped flux concentrator 374. The flux concentrator 374 defines a first tine 376 about which the wound coil 324 extends and a second tine 378 (free of the wound coil). The flux concentrator 374 alters the magnetic field generated by the wound coil 324 so that it is concentrated and confined about the concentrator material. Thus, while the wound coil 324 is helical in shape, the magnetic field generated by the wound coil 324 in combination with the U-shaped flux concentrator 374 can be similar to an induction coil defining two tines, such as shown in FIG. 5. By way of example, and not by limitation, suitable flux concentrator materials include AlphaFlux™ available from Alpha1 of Columbus, Ohio; Fluxtrol® available from Fluxtrol Inc. of Auburn Hills, Mich.; and ferrite materials. The induction coil configuration shown in FIG. 6 is similarly suitable for being placed about an implant and permitting the implant to move through the tines 376, 378 of the induction 'coil' as it deforms upon shape change.

Figure 7:
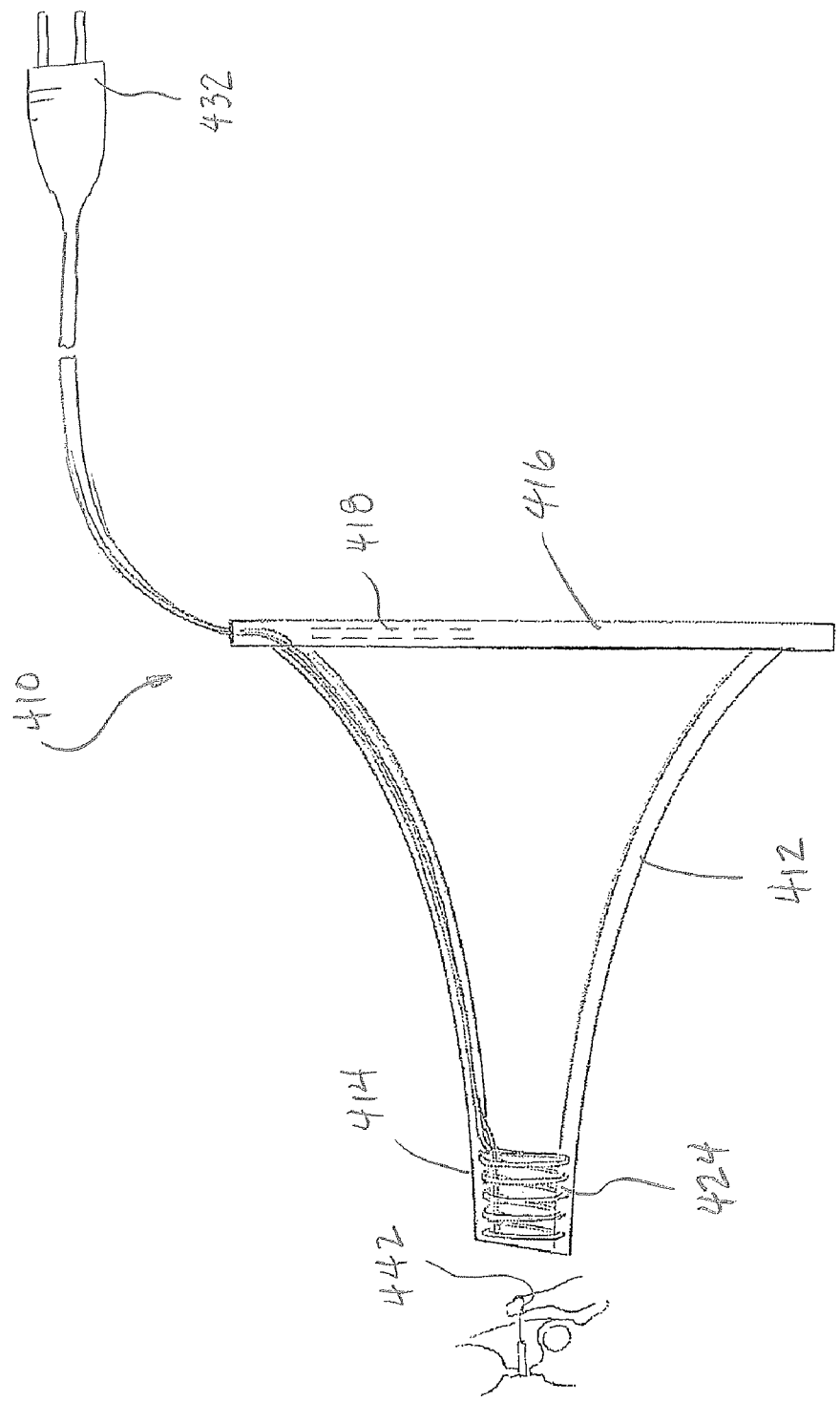
FIG. 7 is a second embodiment of a distal end of an induction heater system according to the invention.

Referring now to FIG. 7, another embodiment of an induction coil heater system 410 includes a speculum 412, and an induction coil 424 provided in the distal end 414 of the speculum. The coil is electrically coupled to a male plug 432 which can be engaged with the female plug 34 of the AC induction power source 14 and optional footswitch 16 to activate the power source, shown with respect to FIG. 1. The speculum 412 is preferably sized for insertion into a human ear and the rim 416 of the speculum may include structure, such as an resilient engagement rib 418, for attachment to an otoscope. Alternatively, the speculum can be used independently of a connected illumination instrument as it is self-supporting in the ear, resting over the bony part of the meatus. When the speculum is inserted into the ear, the distal end 414 of the speculum, and thus the induction coil 424 extending within the distal end of the speculum, are both preferably located within 5-8 mm of the implant 442. When the AC power supply is activated, a magnetic field generated by the coil causes inductive heating of the implant 442 and consequent shape change thereof.

Figure 8:
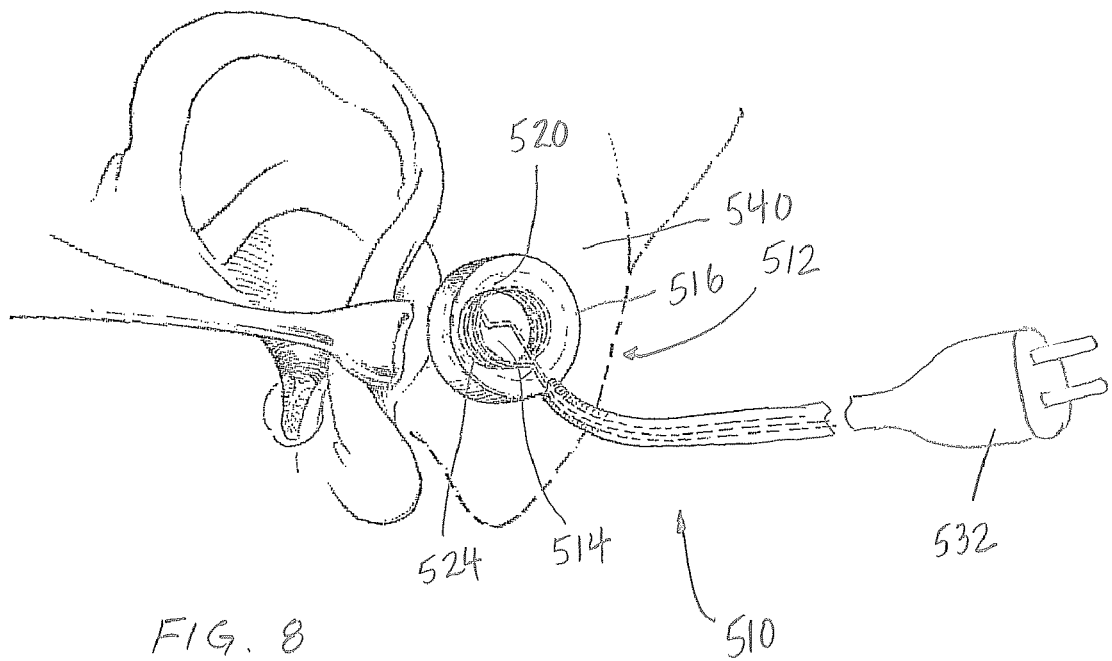
FIG. 8 is a third embodiment of a distal end of an induction heater system according to the invention, shown mounted over the temporal bone.
Figure 9:
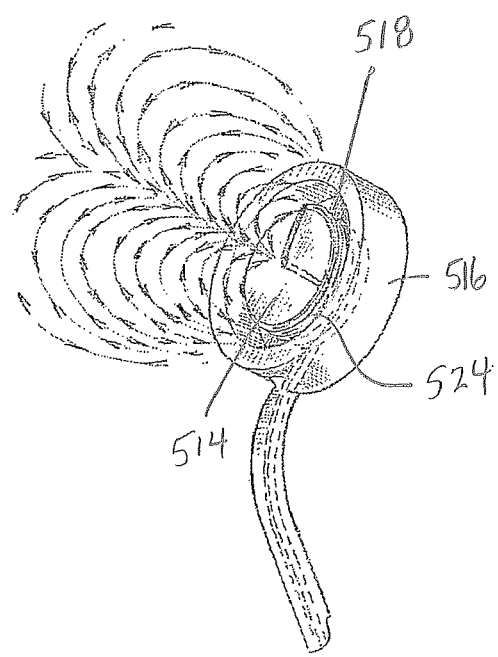
FIG. 9 illustrates, in a bottom perspective view, the magnetic field generated by the induction coil of FIG. 8.

Turning now to FIGS. 8 and 9, another embodiment of an induction coil heater system 510 is partially shown, with an induction coil mount 512 positioned externally over the temporal bone 540 at the middle ear. The mount 512 preferably includes a disc 514 about which the induction coil 524 extends and a ring 516 surrounding the coil. The ring may be a non-metal, a metal, a flux-concentrator material, or a magnetic shielding material adapted to shield the magnetic field generated by the coil. Suitable magnetic shielding materials include Alphaflux™, Fluxtrol®, and ferrite materials as the use of such materials can limit the location of the magnetic field as well by confining and focusing the field. The mount 520 also includes an upper disc 518 (shown removed in FIG. 8) and an a lower disc 520 (shown removed in FIG. 9), each extending across the upper and lower surfaces of the ring 516. The lower disc 520 may be provided with a medical grade adhesive that permits temporary positioning of the mount 512 on the skin of the human body during a surgical procedure and is readily removable thereafter. This permits the induction coil 524 to be stabilized on the exterior of the body in a hands-free manner during the surgical procedure. The coil is coupled via plug 532 to the AC power supply 14 (FIG. 1), as in prior embodiments.

More particularly, the same induction power source 14 is preferably adapted to supply power to each of the embodiments described above. The power source 14 is preferably capable of operating at a frequency of 300 kHz to 1 Mhz at under 100 W. It may be necessary, although is not necessarily required, to alter the power and/or frequency of the power source depending on the configuration of the induction coil or the size and shape of the Nitinol implant. Referring back to FIG. 1, in a first manual mode, the power source preferably includes one or more manual controls 600 to set the desired parameters for the power relative to the induction coil coupled thereto. In a second auto sensing mode, activated by control 602, the power source automatically senses the configuration of the induction coil coupled thereto (i.e., whether for the handpiece, the shape and materials of the coil, the speculum or the body mount). The autosensing can be performed, e.g., at the connector 34, wherein a mechanical, electrical or electronic connection at the connector identifies the specific induction coil device attached thereto, and the corresponding coil configuration. Alternately, the power supply can be programmed to sense the induction characteristics of the coil and adjust settings accordingly. Once the coil configuration is sensed, the power source automatically sets a default power setting for the coil configuration, which can then be modified by the surgeon.

In addition, the power source 14 may operated to pulse RF energy to the induction coil. By way of example, three 80 to 100 watt pulses, each for 0.2 to 0.3 seconds with wait periods of 0.5 to 1.0 seconds between pulses are applied to the induction coil. This results in effective activation of the Nitinol implant with reduced heat generation from the coil. The significant differences in the thermal characteristics of the Nitinol implant (Specific Heat of Nitinol: 0.837 J/g/K; Thermal Conductivity of Nitinol: 0.18 W/cm/K austenite and 0.086 W/cm/K martensite) relative to the copper of the induction coil (Specific Heat of copper: 0.385 J/g/K; Thermal Conductivity of copper: 4 W/cm/K) allow the copper to cool more rapidly and with less energy removal per degree cooled than Nitinol. As a result, the copper induction coil cools much faster than the Nitinol implant during the off phase. Therefore, a pulsed energy activation profile reduces the heat in the induction coil and limits the potential for inadvertent collateral damage to surrounding tissue.

There have been described and illustrated herein several embodiments of a induction heater system and a method of heating a medical implant using induction heating. While particular embodiments of the invention have been described, it is not intended that the invention be limited thereto, as it is intended that the invention be as broad in scope as the art will allow and that the specification be read likewise. Thus, while particular induction heater coil configurations have been disclosed, it will be appreciated that other coil configurations can be used as well. In addition, while particular materials have been disclosed, it will be understood that other materials can be used as well. Moreover, while the induction coil devices have been described with respect to the example of activating an otological middle ear prosthesis, it is appreciated that it may be used to activate and stably implant a shape memory alloy device other than a prosthesis, such as an incudostapedial joint or an active hearing device. It will also be appreciated that the induction coil devices disclosed herein can be used to activate implants within the body at locations other than at the middle ear. Further, while the method ash been described with insertion of an embodiment of the induction heater into a natural orifice, the ear, it will be appreciated that the probe and tip at the end of the handpiece are suitable for insertion into other natural orifices, including the mouth, nasal passages, throat and rectum. In addition, the probe may be inserted into the opening of a surgical wound or through a trocar port, laparoscopic port, or incorporated into a endoscopic instrument. It will therefore be appreciated by those skilled in the art that yet other modifications could be made to the provided invention without deviating from its spirit and scope as claimed.

What is claimed is:

1. A system, comprising:
   a) an ossicular prosthesis implantable in the middle ear, said prosthesis comprising a shape memory portion, wherein upon heat activation to a phase transformation temperature, said shape memory portion changes from a first configuration to a second configuration; and
   b) an induction heater system for heat activation of said shape memory portion, said induction heater system comprising,
      i) a user-manipulable handle,
      ii) a elongate probe extending from said handle, said probe having a distal tip extending along a longitudinal axis and having a diameter of between 0.3 mm and 2.0 mm to allow insertion into a small surgical opening,
      iii) an induction coil coupled to said distal tip and displaced from said handle by said probe, said induction coil made of an electrically conductive material, said induction coil having a dimension in a direction transverse to the longitudinal axis that does not exceed 4 mm, and
      iv) a first connector for coupling said induction coil to an alternating current radio frequency induction power supply,
   wherein said handle is adapted for a surgeon to manually engage the handle to support and manipulate the probe and induction coil during an operation.

2. A system according to claim 1, wherein:
said shape memory portion comprises nickel-titanium.

3. A system according to claim 1, wherein:
said coil comprises copper.

4. A system according to claim 1, wherein:
said coil consists essentially of three to fifteen windings.

5. A system according to claim 1, wherein:
said coil includes an insulative sheath.

6. A system according to claim 1, further comprising:
an induction power supply capable of operating at a frequency between 300 KHz and 1MHz, said power supply includes a second connector for connection to said first connector.

7. A system according to claim 1, wherein:
said probe is rigid and includes a proximal end and a distal end, and said proximal and distal ends extend at an angle relative to each other.

8. A system comprising:
   a) an induction heater system including,
      i) a speculum having a larger proximal end and a smaller distal end and an opening extending therethrough,
      ii) an induction coil coupled to said smaller distal end, said induction coil made of an electrically conductive material, and
      iii) a connector for coupling said induction coil to an alternating current radio frequency induction power supply; and
   b) an ossicular prosthesis implantable in the middle ear, said prosthesis comprising a shape memory portion, wherein upon heat activation to a phase transformation temperature by said induction coil, said shape memory portion changes from a first configuration to a second configuration.

9. A system according to claim 8, wherein:
said coil comprises copper.

10. A system according to claim 8, wherein:
said coil consists essentially of three to fifteen windings.

11. A system according to claim 8, wherein:
said coil includes an insulative sheath.

12. A system according to claim 8, further comprising:
an induction power supply capable of operating at a frequency between 300 KHz and 1 MHz, said power supply includes a second connector for connection to said first connector.

13. A system according to claim 6, wherein:
said power supply generates a pulsed energy activation profile that operates to limit heat in said coil which can be transferred to tissue in the middle ear.

14. A system according to claim 1, wherein:
said probe has a proximal portion with a first diameter, and said distal tip has a second diameter smaller than said first diameter, said second diameter less than 2 mm.

15. A system according to claim 14, wherein:
said second diameter is between 0.3 mm and 1.5 mm.

16. A system according to claim 15, wherein:
said probe includes a bend between said proximal portion and said distal tip that angles said proximal portion and said distal tip relative to each other.

17. A system according to claim 16, wherein:
said probe has a length between 20 mm and 70 mm.

* * * * *